(12) United States Patent
Lee

(10) Patent No.: US 8,398,595 B2
(45) Date of Patent: Mar. 19, 2013

(54) INFUSION PUMP

(75) Inventor: Freddie Eng Hwe Lee, Singapore (SG)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 12/835,209

(22) Filed: Jul. 13, 2010

(65) Prior Publication Data

US 2012/0016306 A1      Jan. 19, 2012

(51) Int. Cl.
*A61M 1/00*          (2006.01)

(52) U.S. Cl. ..................... 604/153; 604/98.02

(58) Field of Classification Search .............. 604/153, 604/132, 37, 98.01–98.02, 217, 255, 259, 604/262
See application file for complete search history.

(56) References Cited

U.S. PATENT DOCUMENTS

| | | | | |
|---|---|---|---|---|
| 5,105,983 | A | * | 4/1992 | Sancoff et al. ............. 222/103 |
| 5,284,481 | A | * | 2/1994 | Soika et al. ................ 604/132 |
| 5,360,411 | A |   | 11/1994 | Mimura et al. |
| 6,135,153 | A |   | 10/2000 | Cleland et al. |
| 6,398,760 | B1 | * | 6/2002 | Danby ....................... 604/132 |
| 7,618,432 | B2 | * | 11/2009 | Pedersen et al. ........... 606/194 |
| 7,803,133 | B2 |   | 9/2010 | Lee |
| 8,092,417 | B2 |   | 1/2012 | Kim |
| 2005/0277883 | A1 |   | 12/2005 | Kriesel |
| 2006/0229558 | A1 |   | 10/2006 | Heston et al. |

FOREIGN PATENT DOCUMENTS

| | | |
|---|---|---|
| EP | 0 577 354 | 1/1994 |
| EP | 0 885 620 | 12/1998 |

OTHER PUBLICATIONS

International Search Report for PCT/IB2011/001621 dated Jan. 19, 2012.
International Search Report for PCT/IB2011/001660 dated Jan. 27, 2012.

* cited by examiner

*Primary Examiner* — Nicholas Lucchesi
*Assistant Examiner* — Melissa A Snyder
(74) *Attorney, Agent, or Firm* — RatnerPrestia

(57) ABSTRACT

An apparatus for delivering fluid at a substantially constant flow rate includes a pair of substantially rigid surface elements for defining a volume that is variable according to constrained separation of the pair of surface elements. The apparatus further includes a support member disposed within the volume defined by the pair of surface elements; and a holding reservoir disposed within the volume defined by the pair of surface elements. The holding reservoir is attachably fastened at a first end to the support member and attachably coupled at a second end to the pair of surface elements.

26 Claims, 6 Drawing Sheets

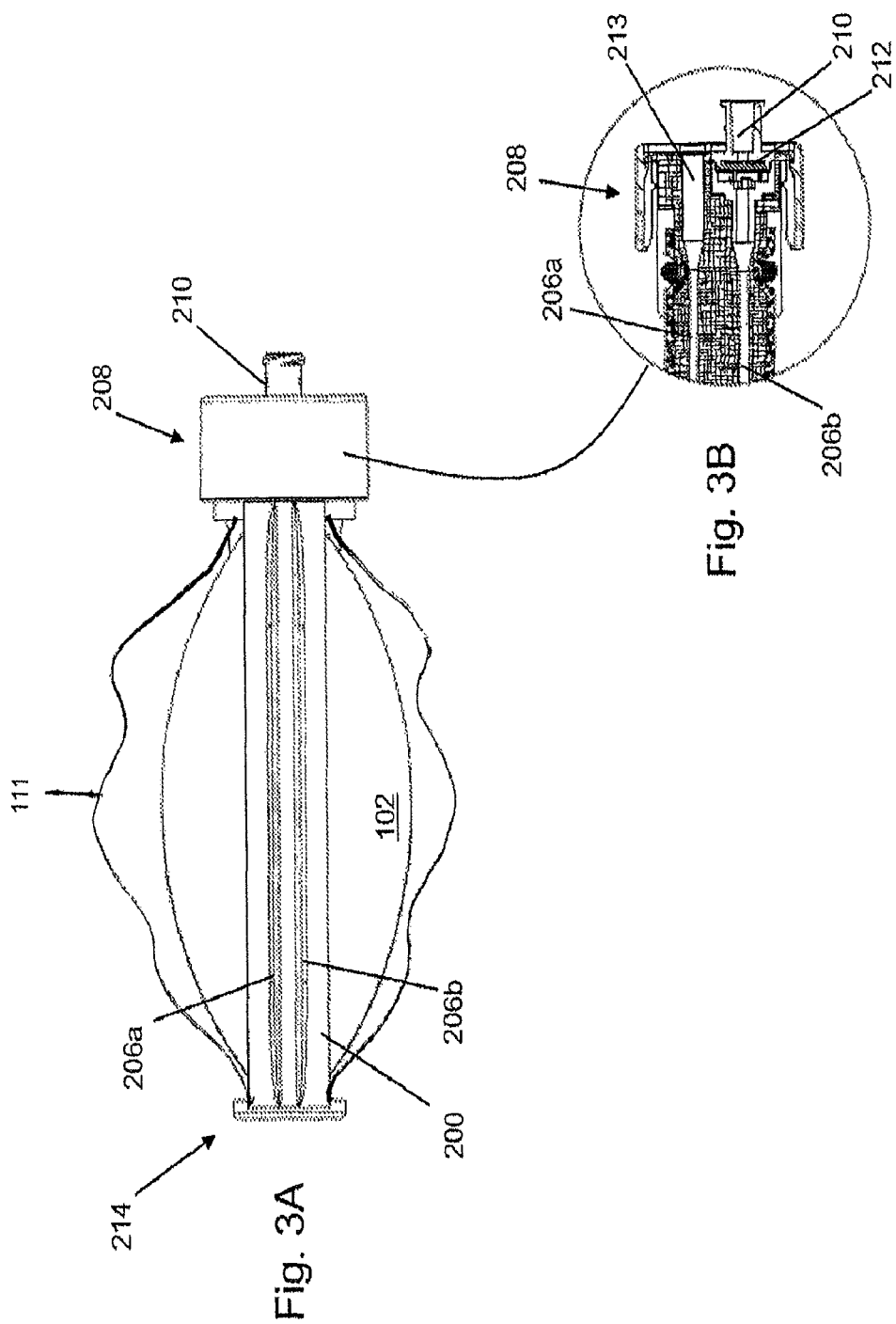

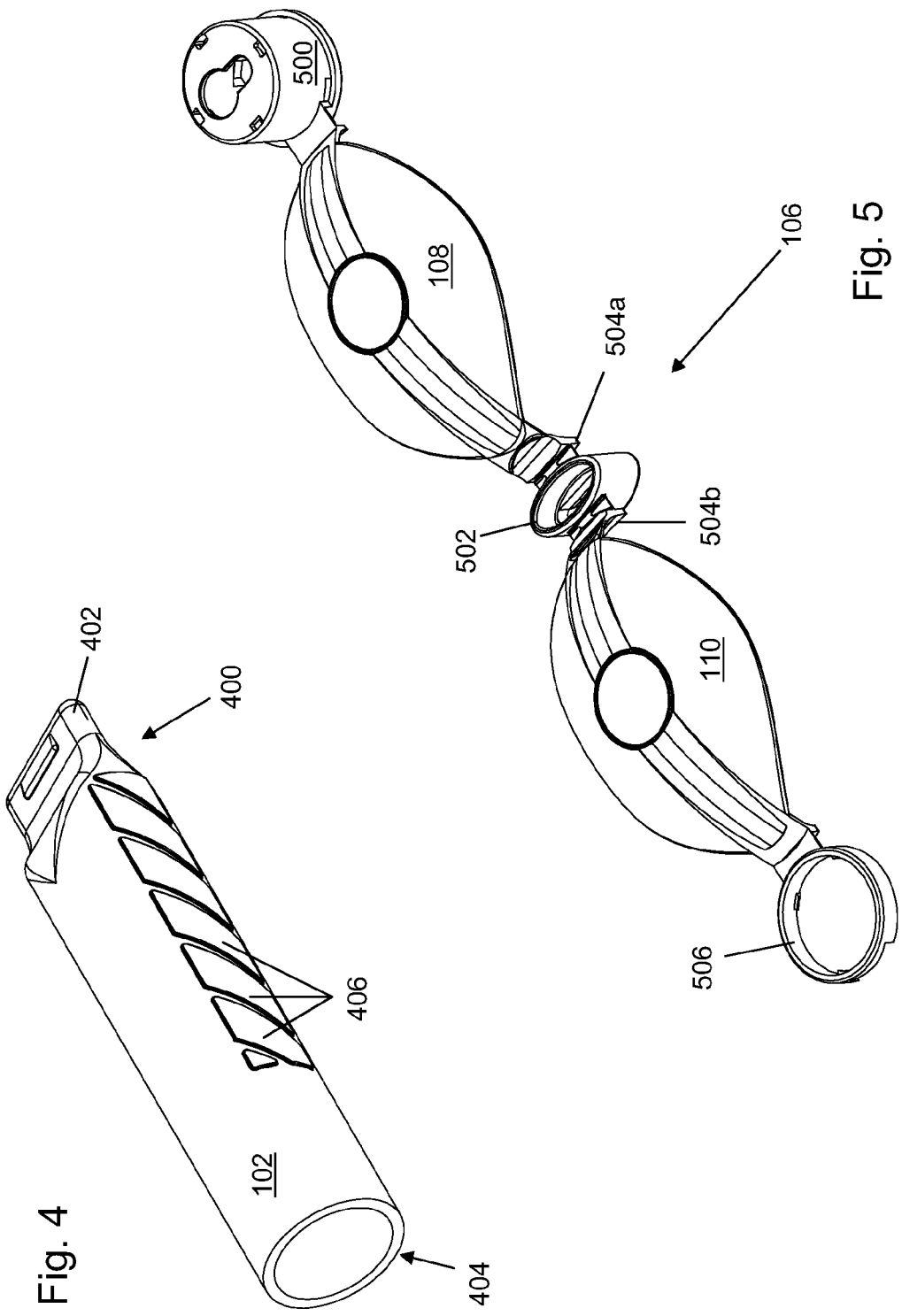

INFUSION PUMP

BACKGROUND

Elastomeric pumps are widely used in healthcare settings to deliver fluids and medication to patients. In some pumps, fluid is stored in a drug reservoir or bladder made of silicon or another rubber polymer and attached to a central support core. When filled, the bladder expands and the increased surface area of the bladder stores energy that exerts pressure on the fluid, driving the fluid out of the bladder. The flow rate of the fluid is often limited by a restricting orifice such as a glass capillary or a section of PVC tubing.

The symmetry and geometry of the bladder when filled affects the pressure exerted on the fluid therein and thus the flow profile of the fluid delivered from the pump. To constrain the expansion of the bladder, the bladder is often enclosed in an outer cover that restricts its asymmetrical expansion, such as a rigid cover or a flexible and non-expandable cover. In other types of pumps, the bladder is affixed to a sliding core, which helps to control the symmetry and geometry of the expanded bladder. In some pumps, the bladder is formed of a rubber polymer that exerts force on the fluid therein and a silicone lining on the inside of the bladder that prevents the fluid from coming into contact with the rubber polymer.

SUMMARY

In a general aspect, an apparatus for delivering fluid at a substantially constant flow rate includes a pair of substantially rigid surface elements for defining a volume that is variable according to constrained separation of the pair of surface elements. The apparatus further includes a support member disposed within the volume defined by the pair of surface elements; and a holding reservoir disposed within the volume defined by the pair of surface elements. The holding reservoir is attachably fastened at a first end to the support member and attachably coupled at a second end to the pair of surface elements.

Embodiments may include one or more of the following.

The constrained separation of the pair of surface elements is defined by a hinge assembly operable to transition from a first state to a second state as fluid is introduced to the holding reservoir. The constrained separation of the pair of surface elements is defined by a hinge assembly operable to transition from a first state to a second state when a predetermined fluid pressure within the holding reservoir is reached. The constrained separation of the pair of surface elements is defined by a hinge assembly operable to transition from a second state to a first state as fluid is dispensed from the holding reservoir.

The pair of surface elements are connected by a hinge assembly that includes a receptacle for receiving the second end of the holding reservoir. The hinge assembly is operable to transition from a first state to a second state, thereby enabling expansion of the holding reservoir along a longitudinal dimension defined by a distance between the first end and the second end of the holding reservoir. The hinge assembly is operable to transition from a second state to a first state, thereby enabling contraction of the holding reservoir along a longitudinal dimension defined by a distance between the first end and the second end of the holding reservoir. The receptacle of the hinge assembly includes a collar configured to have an interference fit with a tab extending from the second end of the holding reservoir.

Radial expansion of the holding reservoir is limited by opposing interior surfaces of the pair of surface elements. A first end of the support member has a chisel tip configuration. A plurality of surface textures are disposed on an outer surface of the holding reservoir. The holding reservoir is mounted on the support member so that an interior surface of the holding reservoir in a non-pressurized state contacts an exterior surface of the support member. The holding reservoir is mounted on the support member so that less than an entirety of an interior surface of the holding reservoir in a pressurized state contacts an exterior surface of the support member.

The apparatus further includes a sleeve disposed about the holding reservoir. The sleeve is formed of a material that restricts transmission of at least some wavelengths of light. The sleeve is a sheath having a tight fit about the holding reservoir.

The holding reservoir is configured to expand substantially symmetrically about the support member.

The support member is a generally cylindrical fixed-length support member that is attachably fastened at a first end to the pair of surface elements. A second end of the support member extends through the volume defined by the pair of surface elements without coming into contact with any portion of the pair of surface elements. The first end of the holding reservoir is attachably fastened to the first end of the support member.

In another general aspect, an infusion pump includes a pair of substantially rigid surface elements for defining a volume that is variable according to constrained separation of the pair of surface elements. The infusion pump further includes a generally cylindrical fixed-length support member disposed within the volume defined by the pair of surface elements. A first end of the support member is attachably fastened to the pair of surface elements and a second end of the support member extends through the volume defined by the surface elements without coming into contact with any portion of the pair of surface elements. The infusion pump also includes a holding reservoir disposed within the volume defined by the pair of surface elements. A first end of the holding reservoir is attachably fastened to the first end of the support member and a second end of the holding reservoir is attachably coupled to the pair of surface elements.

In another general aspect, an infusion pump includes a support member; a holding reservoir mounted on the support member; and a holding reservoir limiter that includes a pair of substantially rigid surface elements for defining a volume within which the holding reservoir is disposed. The volume is variable according to constrained separation of the pair of surface elements.

Embodiments may include one or more of the following.

The holding reservoir limiter includes a hinge assembly that couples respective first ends of the pair of surface elements. The hinge assembly includes a collar to which a first hinge and a second hinge are coupled. The holding reservoir limiter includes a terminal assembly that couples respective second ends of the pair of surface elements. The terminal assembly includes a ring and a cap.

Among other advantages and features, the infusion pump described herein can provide one or more of the following advantages.

The symmetrical radial expansion of the bladder of the infusion pump coupled with the additional degree of freedom provided by the axial expansion exerts a uniform pressure on the fluid within the pump and thus results in a consistent flow profile. More particularly, the infusion pump is capable of delivering fluid with a reduced or eliminated initial spike in flow rate and with a constant flow rate throughout the duration of the infusion.

The infusion pump described herein is widely applicable for patients receiving intravenous, percutaneous, subcutaneous, intra-operative sites, or epidural administration of medication. No battery and no main supply is needed; thus, a patient receiving an infusion can be ambulatory and is free from risks associated with device power failure.

The flow rate is only minimally dependent on temperature (e.g., about 1.5% change in flow rate per degree Celsius) and is unaffected by the storage time of the pump after filling. Furthermore, the intra-device variability is minimal because the expansion of the bladder, and hence the pressure applied to the fluid contained therein, is consistent among like devices.

The infusion pump described herein can be manufactured from hypoallergenic materials that are compatible with a wide range of drugs, including antibiotics, analgesics, and cytostatic drugs.

Other features and advantages of the invention are apparent from the following description and from the claims.

BRIEF DESCRIPTION OF DRAWINGS

FIG. 3A is a cross-sectional diagram of the infusion pump.
FIG. 3B is a cross-sectional diagram of an end of the infusion pump.
FIG. 4 is an illustration of the bladder of the infusion pump.
FIG. 5 is an illustration of the harness belt.

DETAILED DESCRIPTION

Figure 1A:
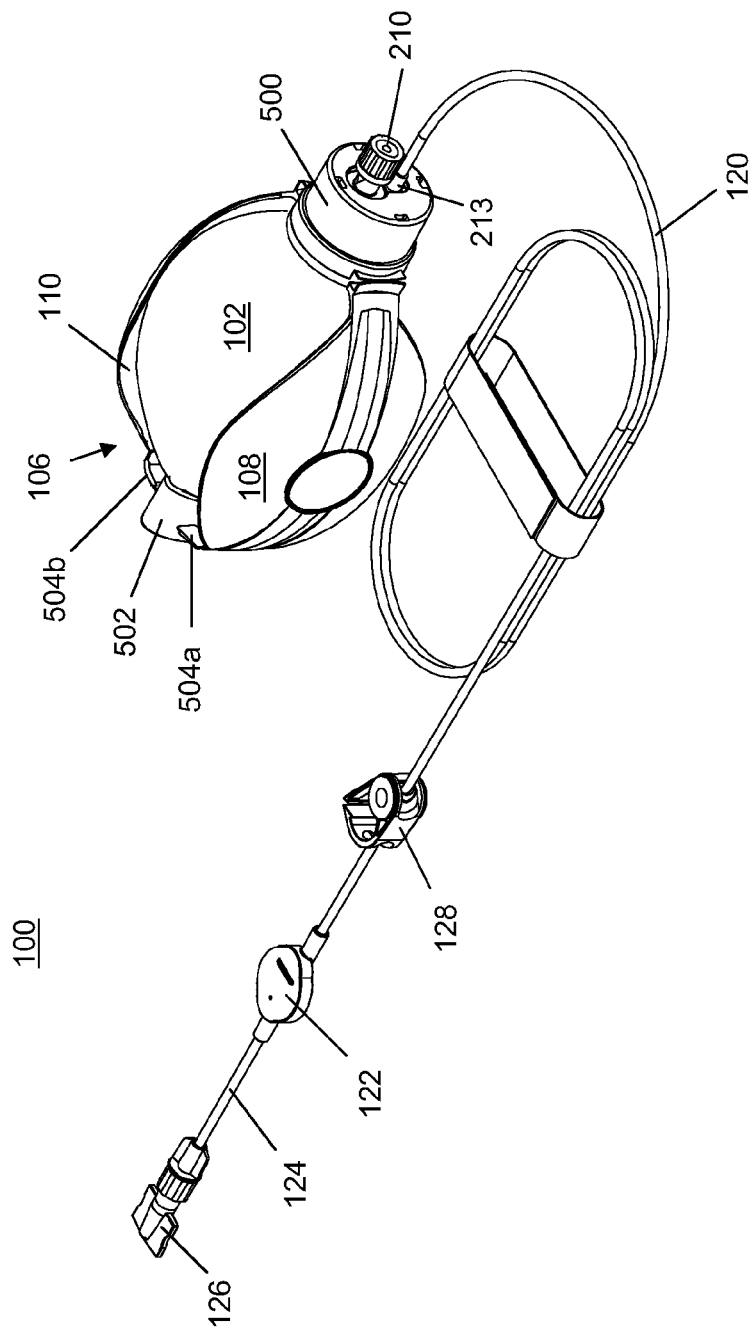
FIG. 1A is an illustration of an infusion pump in a filled state.
Figure 1B:
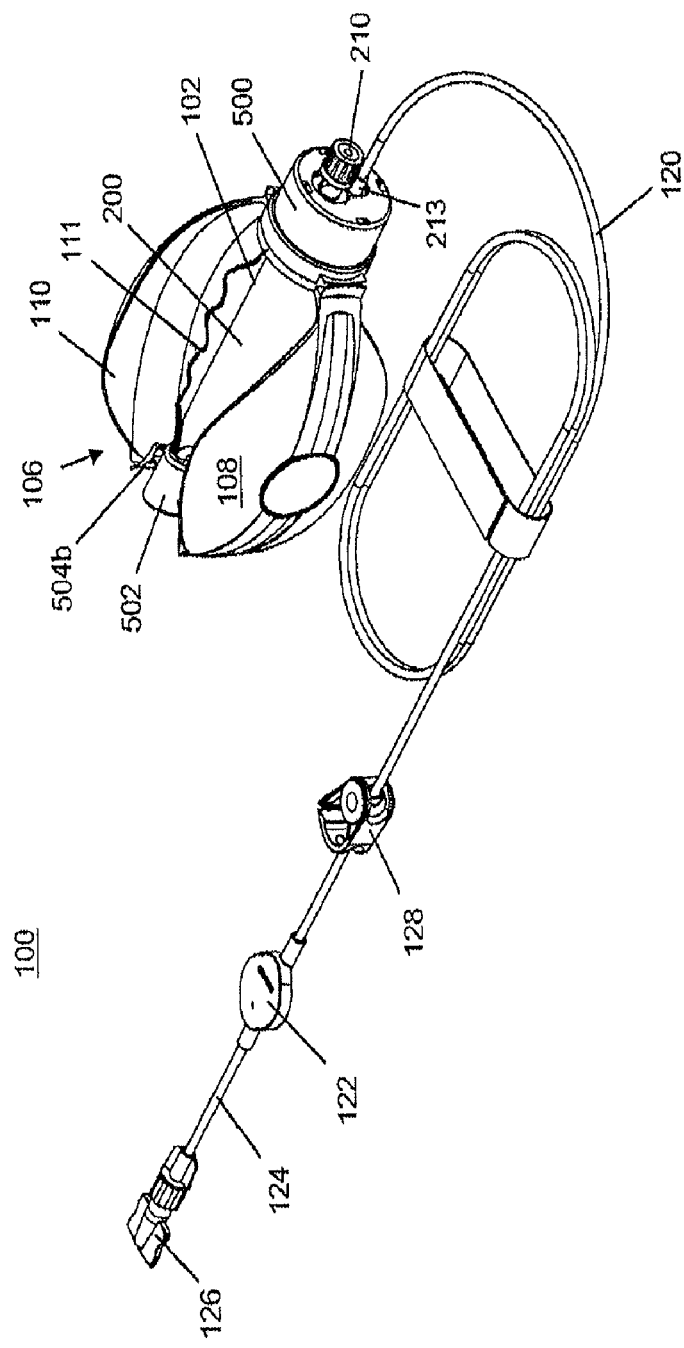
FIG. 1B is an illustration of the infusion pump of FIG. 1A in an empty state.

Referring to FIGS. 1A and 1B, an infusion pump 100 is a portable and disposable device used to deliver fluids, such as a fluid containing an antibiotic drug to be administered to a patient in a healthcare setting. In a filled state (FIG. 1A), a bladder 102 is expanded and full of fluid; in an empty state (FIG. 1B), the bladder is collapsed. When fully or partially filled, the bladder exerts pressure on the fluid therein, contracting substantially symmetrically and forcing the fluid out of the bladder. A harness belt 106, formed of a first side shield 108 and a second side shield 110, partially surrounds the bladder.

Figure 2:
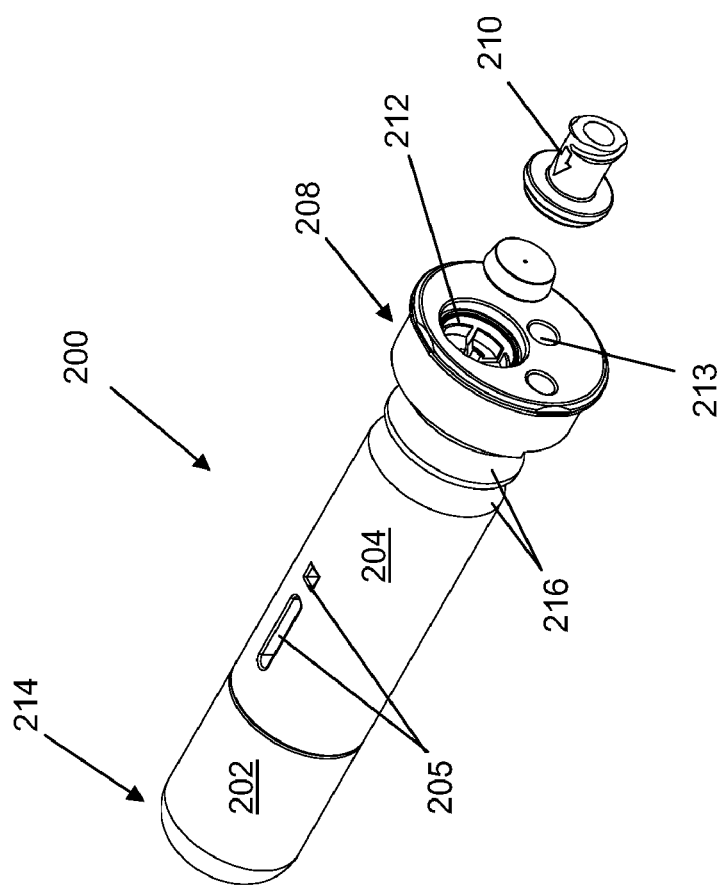
FIG. 2 is an illustration of the support core of the infusion pump.

Referring also to FIGS. 2, 3A, and 3B, bladder 102 is disposed around a support core 200. Support core 200 is a fixed-length, generally cylindrical member formed by inserting an inner support core 202 into an annular cavity of an outer support core 204. Tabs (not shown) on the inner support core insert into openings 205 on the outer support core, causing the inner and outer support core to lock together. Two flow paths 206a, 206b extend within support core 200. At a proximal end 208 of the support core, a filling port 210 in fluid communication with flow path 206a incorporates a one-way anti-siphon value 212 to prevent leakage of fluid during and after filling of the pump. Fluids are delivered from the pump via an output port 213 in fluid communication with flow path 206b. A distal end 214, which is closed, is generally shaped like a chisel tip.

Referring to FIG. 4, bladder 102 is formed of a single-layer flexible membrane. In its fully deflated (i.e., empty) state, the bladder has a generally cylindrical shape which tapers at its closed end to form a chisel tip 400. A tap 402 extending from the end of chisel tip 400 is sized and dimensioned to have a slight interference fit with a collar of harness belt 106, as discussed below (see, e.g., FIGS. 4 and 5).

Bladder 102 is mounted onto support core 200 by sliding an open end 404 of the bladder along the length of the support core, starting at the distal end 214 of the support core. Only the open end 404 of the bladder is affixed to the support core; no other portion of the bladder is attached to the support core. Support core 200 has circular grooves 216 (see FIG. 2) near its proximal end 208 into which a portion of bladder 102 can be biased using a pair of o-rings (not shown).

When infusion pump 100 is filled with fluid, bladder 102 expands radially and substantially symmetrically away from support core 200. At a certain point, the bladder also begins to expand axially away from the distal end 214 of the support core. As fluid is delivered from the bladder, the chisel tip shape of distal end 116 helps the bladder to glide back to its original, deflated position.

In some cases, bladder 102 includes surface textures 406, e.g., along opposing portions of a middle segment of the cylindrical body of the bladder. In its fully deflated state, the thickness of the bladder wall is generally constant except where surface textures 406 are situated. At these locations, the thickness of the bladder wall is increased by the thickness of the surface texture. This relative difference in wall thickness aids in preventing a 'lopsided' expansion of the bladder as it is filled with fluid. Bladders with surface textures are generally mounted onto support core 200 such that the portions of the bladder without the surface textures face side shields 108, 110 while the portions of the bladder with the surface textures face the gaps between the side shields.

Referring to FIG. 5, harness belt 106 is an integrally molded assembly including a cap 500, first side shield 108, second side shield 110, a collar 502, a pair of harness hinges 504a, 504b, and a ring 506. Each side shield 108, 110 is generally shaped like a tortoise shell and provides a surface area for printing manufacturing data and device identification, such as lot numbers, fill volume, flow rates, and flow duration. First side shield 108 is attached at one end to cap 500 and at the other end to collar 502 via harness hinge 504a. Second side shield 110 is attached at one end to ring 506 and at the other end to collar 502 via harness hinge 504b. The cap and the ring are each sized and dimensioned to have a slight interference fit with the proximal end 208 of support core 200.

Figure 6:
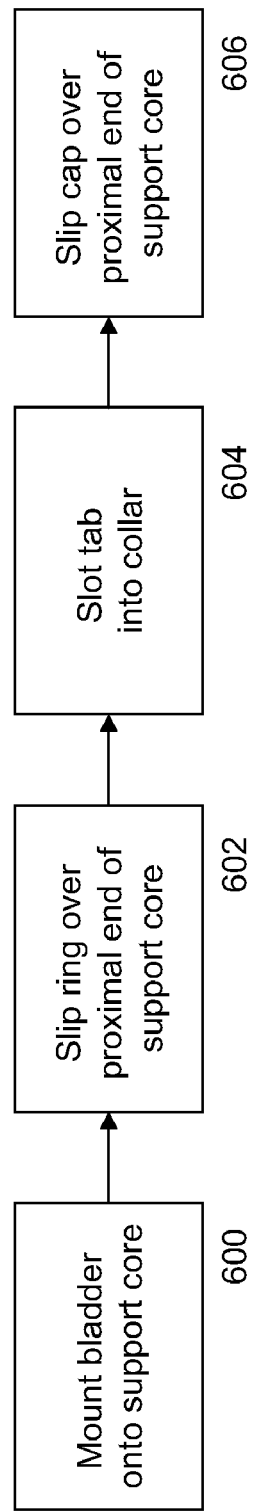
FIG. 6 is a flow chart of the assembly process.

Referring to FIG. 6, to assemble infusion pump 100, bladder 102 is mounted onto support core 200 as described above (step 600). The ring 506 of harness belt 106 is then slipped over the proximal end 208 of the support core (step 602). The tab 402 extending from the chisel tip end 400 of the bladder is slotted into the collar 502 of the harness belt (step 604). Finally, the cap 500 of the harness belt is slipped over the proximal end 208 of the support core, contacting the ring 506 of the harness belt (step 606). In other examples, step 604 may occur prior to step 602. The result of the assembly process is the infusion pump as shown in FIG. 1B.

Referring also to FIGS. 1A and 1B, the design of harness belt 106 and, more particularly, the default positions of harness hinges 504a, 504b restricts the initial axial expansion of bladder 102 as fluids are first introduced into the bladder, instead encouraging radial expansion. As more fluids enter the bladder, the surface textures 406 aid in the symmetric radial expansion of the bladder about support core 200.

As still more fluids enter the bladder, the pressure exerted by the fluids on the inner walls of the bladder causes the chisel tip end 400 of the bladder to push against collar 502 of the harness belt 106 (i.e., away from the distal end 214 of the support core). The harness hinges 504a, 504b gradually flip open as the pressure inside the bladder mounts, and the position of the hinges transitions from that shown in FIG. 1B to that shown in FIG. 1A. In some cases, the bladder is considered to be in its fully filled state once the harness hinges are completely flipped open. In other cases, the maximum amount of fluids that enter the bladder is limited by the side shields 108, 110 of the harness belt.

Referring to FIG. 6, when filled, bladder 102 expands, as discussed above. The increased surface area of the bladder stores energy that exerts pressure on the fluid within, causing the bladder to contract substantially symmetrically about the support core and driving the fluid out of the bladder through output port 213 and into a fluid delivery line 120. The flow rate of the fluid may be limited by a restricting orifice (not shown), such as a glass capillary or a section of PVC tubing. The fluid delivery line can be coupled to other components, such as an air trap 122 with an anti-microbial filter, a microbore restrictor tubing 124, or a patient Luer adapter 126. A clamp 128 is used to start and stop fluid flow.

In an alternative embodiment, a sleeve 111 (FIGS. 1B and 3A) is disposed about the bladder 102. The sleeve 111 may be an amber-colored sheath that is tightly fitted around bladder 102. The sheath expands and contracts along with the bladder as fluids are added to or expelled from the pump. The amber color of the sheath absorbs certain wavelengths of light, reducing the exposure of the fluids stored within bladder 102 to those wavelengths and thus preventing or minimizing degradation and/or decomposition of photosensitive compounds in the fluids.

The infusion pumps are made from hypoallergenic materials that are compatible with a wide range of drugs. For instance, components of the pumps may be made from latex-free materials such as medical grade acrylonitrile butadiene styrene (ABS), polycarbonate, silicone, and di(2-ethylhexyl) phthalate (DEHP)-free polyvinyl chloride (PVC).

It is to be understood that the foregoing description is intended to illustrate and not to limit the scope of the invention, which is defined by the scope of the appended claims. Other embodiments are within the scope of the following claims.

What is claimed is:

1. An apparatus for delivering fluid at a substantially constant flow rate, the apparatus comprising:
   a pair of substantially rigid surface elements for defining a volume that is variable according to constrained separation of the pair of surface elements;
   a support member disposed within and extends through the volume defined by the pair of surface elements; and
   a holding reservoir disposed within the volume defined by the pair of surface elements, the holding reservoir being attachably fastened at a first end to the support member and attachably coupled at a second end to the pair of surface elements by a hinge assembly comprising at least one hinge and a receptacle for receiving the second end of the holding reservoir.

2. The apparatus of claim 1, wherein the constrained separation of the pair of surface elements is defined by the hinge assembly operable to transition from a first state to a second state as fluid is introduced to the holding reservoir.

3. The apparatus of claim 1, wherein the constrained separation of the pair of surface elements is defined by the hinge assembly operable to transition from a first state to a second state when a predetermined fluid pressure within the holding reservoir is reached.

4. The apparatus of claim 1, wherein the constrained separation of the pair of surface elements is defined by the hinge assembly operable to transition from a second state to a first state as fluid is dispensed from the holding reservoir.

5. The apparatus of claim 1, wherein the pair of surface elements are connected by the hinge assembly.

6. The apparatus of claim 5, wherein the hinge assembly is operable to transition from a first state to a second state, thereby enabling expansion of the holding reservoir along a longitudinal dimension defined by a distance between the first end and the second end of the holding reservoir.

7. The apparatus of claim 5, wherein the hinge assembly is operable to transition from a second state to a first state, thereby enabling contraction of the holding reservoir along a longitudinal dimension defined by a distance between the first end and the second end of the holding reservoir.

8. The apparatus of claim 5, wherein the receptacle of the hinge assembly includes a collar configured to have an interference fit with a tab extending from the second end of the holding reservoir.

9. The apparatus of claim 1, wherein radial expansion of the holding reservoir is limited by opposing interior surfaces of the pair of surface elements.

10. The apparatus of claim 1, wherein a first end of the support member has a chisel tip configuration.

11. The apparatus of claim 1, wherein a plurality of surface textures are disposed on an outer surface of the holding reservoir.

12. The apparatus of claim 1, wherein the holding reservoir is mounted on the support member so that an interior surface of the holding reservoir in a non-pressurized state contacts an exterior surface of the support member.

13. The apparatus of claim 1, wherein the holding reservoir is mounted on the support member so that less than an entirety of an interior surface of the holding reservoir in a pressurized state contacts an exterior surface of the support member.

14. The apparatus of claim 1, further comprising a sleeve disposed about the holding reservoir.

15. The apparatus of claim 14, wherein the sleeve is formed of a material that restricts transmission of at least some wavelengths of light.

16. The apparatus of claim 14, wherein the sleeve is a sheath having a tight fit about the holding reservoir.

17. The apparatus of claim 1, wherein the holding reservoir is configured to expand substantially symmetrically about the support member.

18. The apparatus of claim 1, wherein the support member is a generally cylindrical fixed-length support member that is attachably fastened at a first end to the pair of surface elements.

19. The apparatus of claim 18, wherein a second end of the support member extends through the volume defined by the pair of surface elements without coming into contact with any portion of the pair of surface elements.

20. The apparatus of claim 18, wherein the first end of the holding reservoir is attachably fastened to the first end of the support member.

21. An infusion pump comprising:
   a pair of substantially rigid surface elements for defining a volume that is variable according to constrained separation of the pair of surface elements;
   a generally cylindrical fixed-length support member disposed within the volume defined by the pair of surface elements, wherein a first end of the support member is attachably fastened to the pair of surface elements and a second end of the support member extends through the volume defined by the surface elements without coming into contact with any portion of the pair of surface elements; and
   a holding reservoir disposed within the volume defined by the pair of surface elements, wherein a first end of the holding reservoir is attachably fastened to the first end of the support member and a second end of the holding reservoir is attachably coupled to the pair of surface elements by a hinge assembly comprising at least one hinge and a receptacle for receiving the second end of the holding reservoir.

22. An infusion pump comprising:
a support member;
a holding reservoir mounted on the support member; and
a holding reservoir limiter that includes a pair of substantially rigid surface elements for defining a volume within which the holding reservoir is disposed, wherein the volume is variable according to constrained separation of the pair of surface elements and a first end of the holding reservoir is attachably fastened to the first end of the support member and a second end of the holding reservoir is attachably coupled to the pair of surface elements by a hinge assembly comprising at least one hinge and a receptacle for receiving the second end of the holding reservoir, wherein the support member is disposed within and extends through the volume defined by the pair of surface elements.

23. The infusion pump of claim 22, wherein the holding reservoir limiter includes the hinge assembly that couples respective first ends of the pair of surface elements.

24. The infusion pump of claim 23, wherein the hinge assembly includes a collar to which a first hinge and a second hinge are coupled.

25. The infusion pump of claim 22, wherein the holding reservoir limiter includes a terminal assembly that couples respective second ends of the pair of surface elements.

26. The infusion pump of claim 25, wherein the terminal assembly includes a ring and a cap.

\* \* \* \* \*